United States Patent

Yamada et al.

[11] Patent Number: 6,106,782
[45] Date of Patent: Aug. 22, 2000

[54] CHROMATOGRAPH

[75] Inventors: Yoshiaki Yamada, Tsuchiura; Kiyotoshi Mori, Hitachinaka, both of Japan

[73] Assignee: Hitachi, Ltd., Tokyo, Japan

[21] Appl. No.: 09/020,703

[22] Filed: Feb. 9, 1998

[30] Foreign Application Priority Data

Feb. 13, 1997  [JP]  Japan .................................... 9-028592

[51] Int. Cl.[7] .......................... G01N 30/00; G06F 13/00; B01D 15/08
[52] U.S. Cl. .............................. 422/70; 422/89; 73/23.36; 73/61.52; 96/103; 700/266; 702/30; 702/31; 702/32
[58] Field of Search ....................... 422/70, 89; 73/23.36, 73/23.4, 61.57, 61.58, 23.35, 61.52; 436/161; 364/710.01; 96/102, 103; 700/266, 25; 702/22, 23, 24, 27, 30, 31, 32, 189, 193

[56] References Cited

U.S. PATENT DOCUMENTS 5,068,818  11/1991  Uramoto et al. .
5,278,630  1/1994  Maruyama .

FOREIGN PATENT DOCUMENTS 62-291562A  12/1987  Japan .
410288611A  10/1998  Japan .

*Primary Examiner*—Jill Warden
*Assistant Examiner*—Jennifer C. McNeil

[57] ABSTRACT

A chromatograph is provided for accurately identifying components of a sample even with the use of a moving average method for noise reduction. A eluding solution is supplied to a column by a pump. In a sample injector, the sample injected into the column is separated into components by the column, and converted to an electric signal by a detector. A detected output signal is subjected to data processing in a data processor. The output signal is sampled at regular intervals and subjected to moving average processing in the detector. A sample injection signal from the sample injector is sent to the detector which generates a data processing start signal that is delayed by a time equal to a delay resulting from the moving average processing for the signal. The data processing start signal is sent to the data processor which starts the data processing in response to this signal.

6 Claims, 3 Drawing Sheets

CHROMATOGRAPH

BACKGROUND OF THE INVENTION

1. Field of the Invention

The present invention relates to a chromatograph, and more particularly to a chromatograph which utilizes a moving average method to reduce noise in data.

2. Description of the Related Art

For noise reduction, there are the following three methods which are generally used in chromatography:

A first method employs a RC circuit composed of a coil and a capacitor in an analog signal output stage to reduce short-cycle noise.

A second method converts an analog signal to a digital signal which is then subjected to exponential smoothing, having a similar effect to the RC circuit, to derive an output.

A third method, as shown in JP-A-62-291562, converts an analog signal to a digital signal, and then applies a moving average method using a plurality of data points of the digital signal for noise reduction, after which an output is derived. For an equation used in the moving average, a Savostzky & Golay's equation or the like is suitable.

When the first and second techniques employ a circuit or a smoothing equation providing a large noise reduction effect, distortion is also introduced into necessary signals, thereby causing a degradation in signal separation. In addition, such a circuit or a smoothing equation also reduces a signal height (peak height), so that an improved signal-to-noise ratio (hereinafter referred to as the "S/N ratio"), which is the essential object of the techniques, cannot be achieved.

The third technique samples an analog signal at regular intervals to convert it to a digital signal, wherein digital samples at a predetermined number of sampling points before and after each sampling point are averaged at every sampling time. This technique can reduce noise without introducing distortion in necessary signals and accordingly improve the S/N ratio by appropriately increasing the number of data samples used in the moving average or increasing the data interval (sampling interval).

However, the third method suffers from a delay in an output signal with respect to a true signal. For example, when the moving average is applied using 11 data samples at sampling points spaced by a sampling interval of 100 ms, an output signal is delayed by 500 ms from a true signal (later described). Particularly, as the number of data points (the number of samples) used in the moving average is increased to have a larger noise reduction effect, the delay also becomes larger. Also, when the noise reduction effect is frequently changed, the delay time similarly changes frequently from the true signal.

The chromatograph uses a holding time for identifying components of a sample. The holding time extends from the time a sample is injected into a column and components of the sample are eluded from the column to the time the components are observed as peaks. Therefore, a delay in providing output data, and particularly a varying delay due to a change in the measuring characteristics would hinder accurate identification.

SUMMARY OF THE INVENTION

It is an object of the present invention to provide a chromatograph which is capable of accurately identifying components of a sample, in spite of the use of a moving average method for noise reduction.

To achieve the above object, the present invention provides a chromatograph, wherein a mobile phase is supplied to a column and a sample is injected into the column to separate the sample into components by the column, the separated components are detected to generate an electric signal, a moving average calculation is applied to the electric signal, and processing for deriving data related to a chromatogram is executed based on the averaged electric signal, the chromatograph being characterized in that the start of the processing is delayed by a delay time for generating the averaged electric signal, which is caused by the moving average calculation.

According to this chromatograph, since the holding time never varies due to a delay for generating the average signal in accordance with the moving average, the object of the present invention is achieved.

DESCRIPTION OF THE PREFERRED EMBODIMENTS

Figure 1:
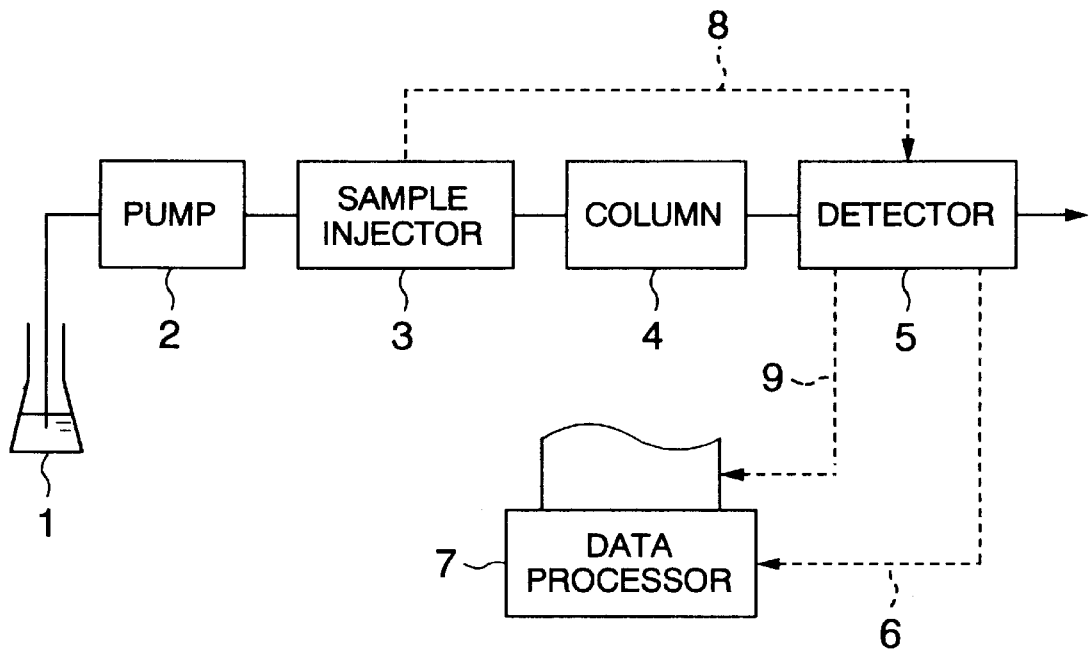
FIG. 1 is a block diagram conceptually illustrating an embodiment of a chromatograph according to the present invention.
Figure 5:
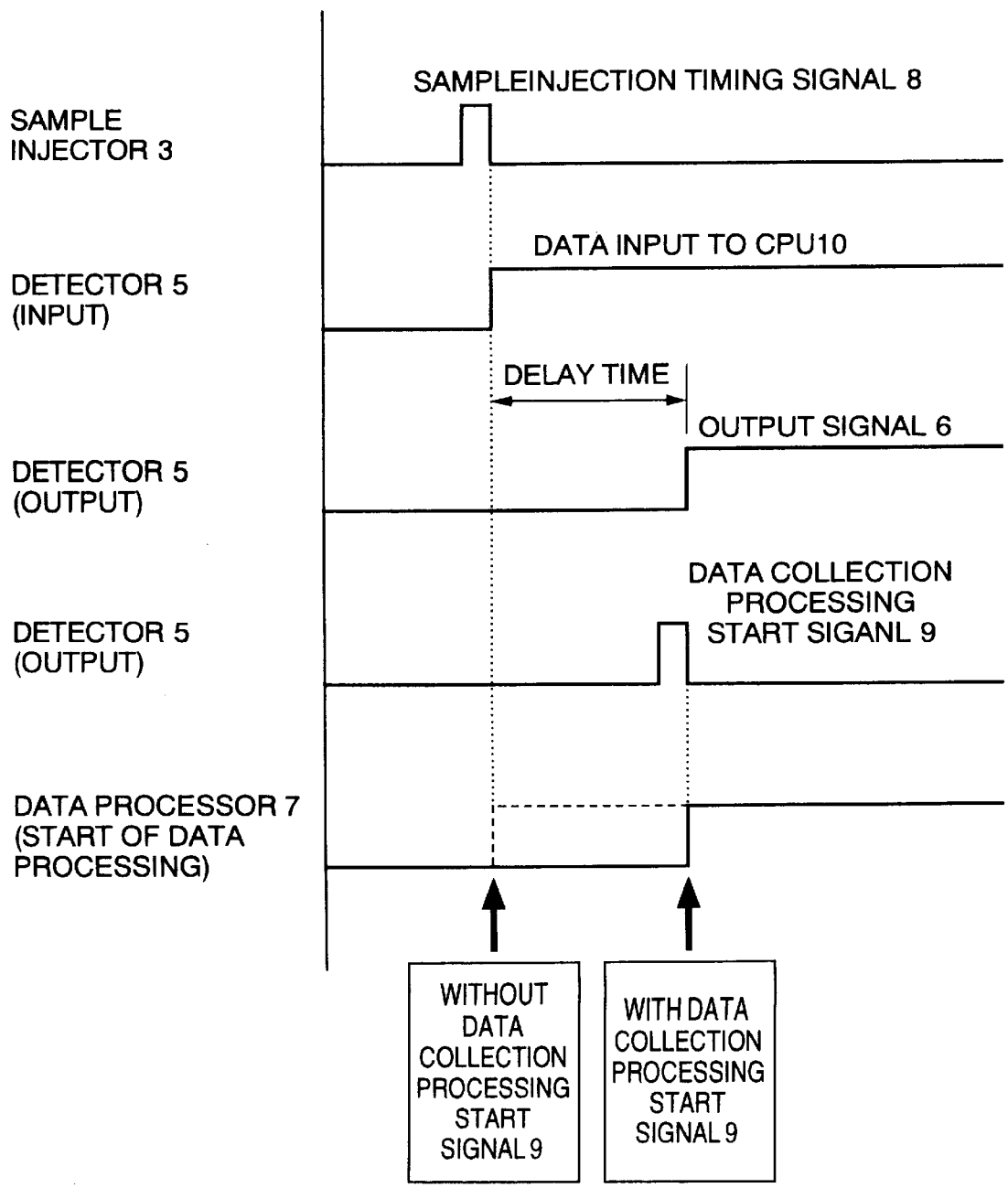
FIG. 5 is a time chart for explaining the operation of the chromatograph according to the present invention.

FIG. 1 illustrates an embodiment of a chromatograph according to the present invention. Solid lines represent a flow of a mobile phase, while dotted lines represent flows of signals. Also, FIG. 5 illustrates a time chart for input and output signals at respective component units of the chromatograph.

An eluting solution, 1 which is a mobile phase, is pressurized by a pump 2 and supplied to a column 4 at a regular flow rate. A sample is injected from a sample injector 3, separated into components by the column 4, and converted to a electric signal by a detector 5. An output signal 6 from the detector 5 is monitored by a data processor 7 which executes processing for deriving data related to so-called chromatogram, such as calculations for the chromatogram, positions and heights of peaks in the chromatogram, and so on. As a result, components are identified by associated peak positions, i.e., times (holding times) from the injection of the sample into the column 4 to the detection of the signal, and the quantitative determination of the respective components can be made from the magnitudes of signal changing amounts (peak heights) observed as peaks.

The foregoing is a general processing operation of the chromatograph. In this embodiment, in addition to the foregoing operation, a sample injection timing signal 8 from the sample injector 3 is sent to the detector 5, such that the sample injection timing signal 8 is based to generate a data collection processing start signal 9, which is delayed by a time equal to a signal delay due to a moving average calculation performed by the detector 5 as noise reduction filtering. The data collection processing start signal 9 is then sent to the data processor 7.

Figure 2:
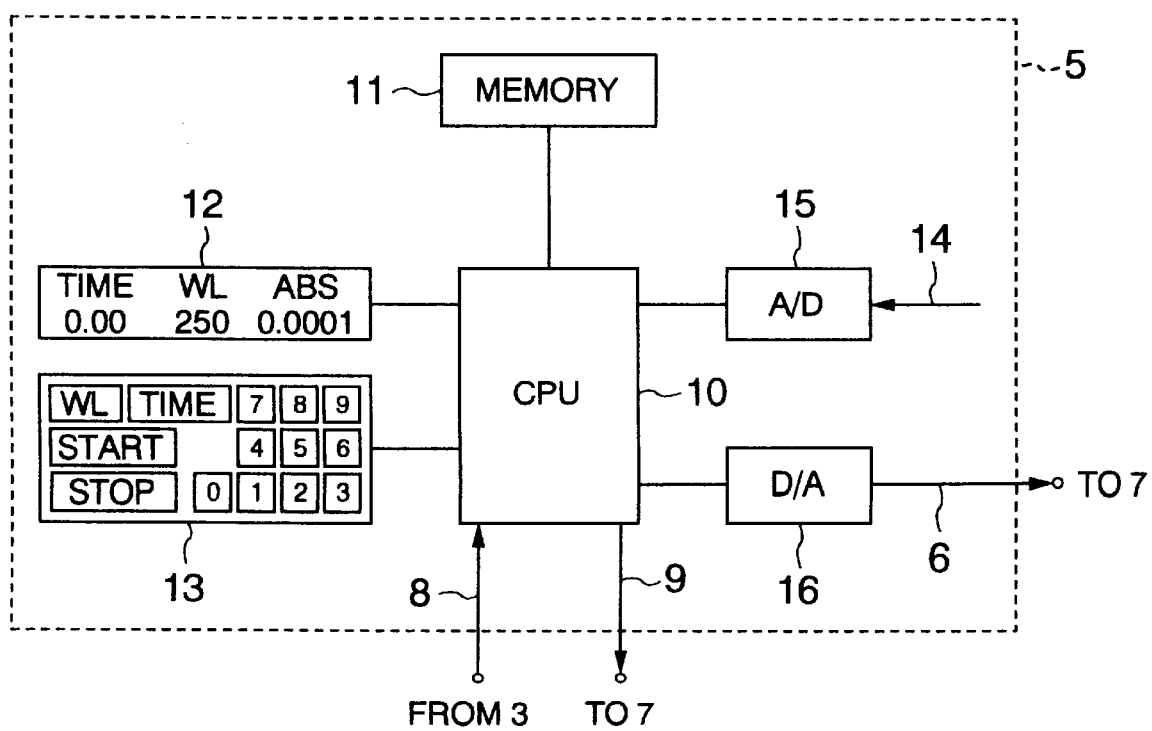
FIG. 2 is a block diagram illustrating a specific configuration of a detector in FIG. 1.

FIG. 2 illustrates a specific configuration of the detector 5 in FIG. 1.

The detector 5 is composed of a CPU 10, a memory 11, a display 12 for displaying signal amounts and set conditions, an input device 13 for inputting measurement conditions including a moving average condition (the number of data points to be averaged =the number of samples), and so on.

A signal 14 indicative of a change in an eluting solution (an absorbance signal when an absorbance detector is used) is sampled by an A/D convertor 15 at regular intervals (here, at intervals of 100 ms) to be converted to a digital signal. The digital signal undergoes a noise reduction in accordance with the moving average method under a moving average condition set by the CPU 10 through the input device 13.

The moving average condition set at the input device 13 is given by setting a time width of data used in the processing involved in the moving average method (hereinafter referred to as the "response time"). For example, assuming that the response time is set to "one second," since the sampling interval is 100 ms, data samples at 11 data points, including five points before and after a current data point, are used in the processing involved in the moving average method. Similarly, when the response time is set to "two seconds," data samples at 21 points are used, and when set to "four seconds," data samples at 41 points are used.

Then, the processed data is converted to an analog signal by a D/A convertor 16, and sent to the data processor 7 as an output signal 6. In this event, the data indicated by the output signal 6 is delayed by a time corresponding to the time taken by performing the noise reduction processing, as compared with data inputted directly from the A/D convertor 15 to the CPU 10 (see FIG. 5). For example, when the response time is set to "one second," since data samples at five points (sampling points) before and after current data are required in addition to the current data, a delay time for the latter five-point portion (500 ms) is added. Generally, while a longer response time provides a larger noise reduction effect, a longer delay time is added to the output signal in proportion to the response time.

Table 1 below shows the output signal from the CPU 10, in the form of a list, when a noise reduction is performed for an input signal (a digital input signal to the CPU 10 after A/D conversion) with the response time set to "one second."

TABLE 1

| Time | Input Signal | Output Signal | |
|---|---|---|---|
| $T_0$ | $D_0$ | | |
| $T_1$ | $D_1$ | | |
| $T_2$ | $D_2$ | | |
| . | . | | |
| . | . | | |
| . | . | ↑ | |
| $T_{N-5}$ | $D_{N-5}$ | | Data Collecting Interval = 100 ms |
| $T_{N-4}$ | $D_{N-4}$ | | |
| $T_{N-3}$ | $D_{N-3}$ | . | ↓ |
| $T_{N-2}$ | $D_{N-2}$ | . | |
| $T_{N-1}$ | $D_{N-1}$ | . | |
| $T_N$ | $D_N$ | $O_{N-5}$ | |
| $T_{N+1}$ | $D_{N+1}$ | $O_{N-4}$ | ↑ |
| $T_{N+2}$ | $D_{N+2}$ | $O_{N-3}$ | Delay in Output Data = 500 ms |
| $T_{N+3}$ | $D_{N+3}$ | $O_{N-2}$ | |
| $T_{N+4}$ | $D_{N+4}$ | $O_{N-1}$ | |
| $T_{N+5}$ | $D_{N+5}$ | $O_N$ | ↓ |
| $T_{N+6}$ | $D_{N+6}$ | $O_{N+1}$ | |
| $T_{N+7}$ | $D_{N+7}$ | $O_{N+2}$ | |
| . | . | . | |

TABLE 1-continued

| Time | Input Signal | Output Signal |
|---|---|---|
| . | . | . |
| . | . | . |

Data Collecting Time Interval = $(T_{N+1} - T_N)$ = 100 ms
Output Signal$(O_N)$ = $(D_{N-5} + D_{N-4} + D_{N-3} + D_{N-2} + D_{N-1} + D_N + D_{N+1} + D_{N+2} + D_{N+3} + D_{N+4} + D_{N+5})/11$ As mentioned above, for acquiring a one-second portion of data, input samples of a total of 11 points, i.e., five points each before and after the reference input timing of data subjected to the averaging, and the input sample at the reference input timing, are averaged and outputted, when the sampling interval is set to 100 ms. More specifically, assuming that a time $T_n$ is a reference point, input samples ($D_{n-5}$ to $D_{n+5}$) at 11 sampling points from $T_{n-5}$ to $T_{n+5}$ are added together, and the sum is divided by "11" to derive an output signal On. In this processing, since 11 data samples are added and divided by 11 to derive an average value, a noise value is theoretically reduced to one over a square root of 11.

In this event, a signal delay time corresponding to five point intervals (500 ms) occurs between the input signal $D_n$ and the output signal $O_n$, as shown in Table 1. Similarly, a delay of one second, corresponding to ten point intervals, occurs when the response time is set to "two seconds," and a delay of two seconds, corresponding to 20 point intervals, occurs when the response time is set to "four seconds." Therefore, if the output signal including a delay time were received by the data processor 7 and subjected to data processing for deriving data related to chromatogram, the output data would be delivered with a holding time increased by the delay time, thereby hindering the identification of components of a sample. (According to the time chart of FIG. 5, the data processor 7 starts the processing at a start time indicated by a broken line.)

To solve this problem, in this embodiment, the sample injector 3 is provided with a means for generating the sample injection timing signal 8 such that the sample injection timing signal 8 is inputted to the detector 5 in response to the injection of a sample into the sample injector 3. The detector 5, in turn, is provided with a means responsive to the sample injection timing signal 8, inputted to the detector 5, for generating the data collection processing start signal 9 at an interval of a delay time calculated from a previously set response time, so that the detector 5 outputs the data collection processing start signal 9 together with the output signal 6 to the data processor 7.

Then, the data processor 7 validates the output signal 6 only after the data collection processing start signal 6 is inputted thereto, and starts the data processing involved in chromatogram. (According to the time chart of FIG. 5, the data processor 7 starts the processing at a start time indicated by a solid line.)

The delay interval between the output timing of the data collection processing start signal 9 and the sample injection timing signal 8 is uniquely determined if the sampling interval and the number of samples (response time) are given. (In this embodiment, since the sampling interval is 100 ms, the delay interval is 500 ms when the response time is one second; one second when the response time is two seconds; and two seconds when the response time is four seconds.)

Therefore, even if the setting of the response time is frequently changed for adjusting a noise reduction effect, the output timing of the data collection processing start signal 9 can be automatically changed in the detector 5 based on the uniquely determined delay time, thereby making it possible to always create a chromatogram without any delay in the holding time in the data processor 7.

Figure 3:
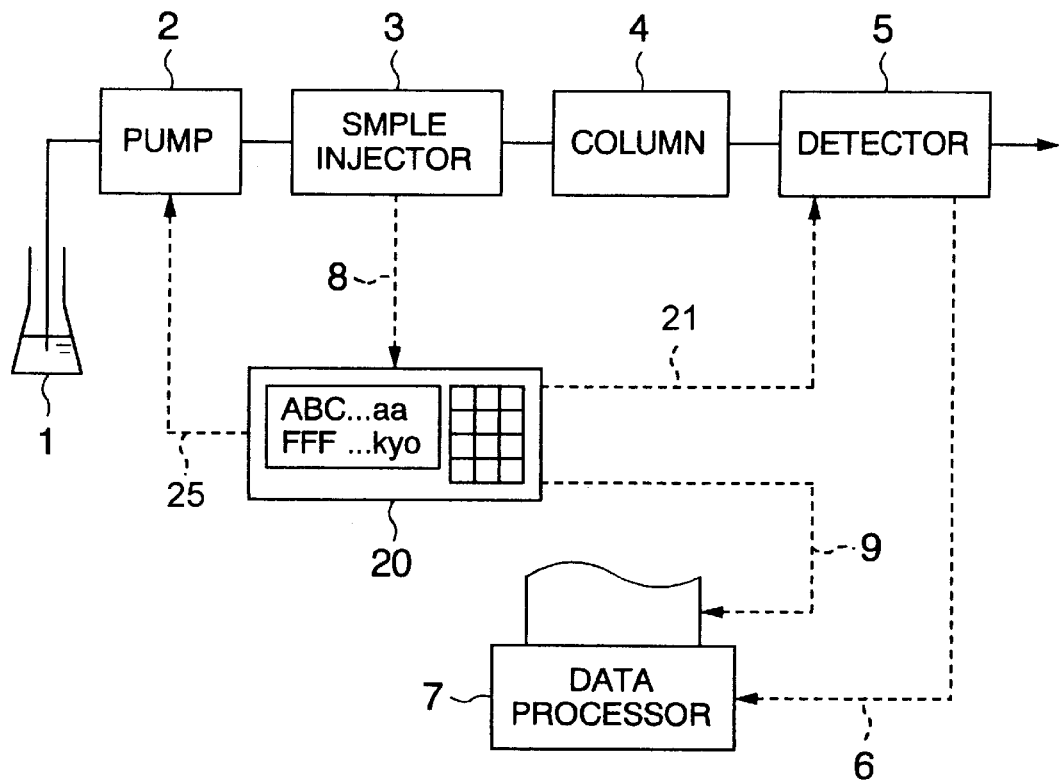
FIG. 3 is a block diagram conceptually illustrating another embodiment of the chromatograph according to the present invention.

FIG. 3 illustrates another embodiment of the chromatograph according to the present invention.

In FIG. 3, solid lines indicate a flow of a mobile phase, while dotted lines indicate flows of signals, similar to FIG. 1. In this embodiment, a controller 20 is provided for controlling a detector 5, a pump 2 and so on. A response time of the detector 5 is set as one of measurement conditions from the controller 20, and sent to the detector 5 as a condition setting signal 21. When a sample injection timing signal 8 is inputted to the controller 20 from a sample injector 3, a gradient start signal 25 is outputted from the controller 20 to the pump 2 in synchronism with the sample injection timing signal 8. A data collection processing start signal 9 is outputted with a delay time corresponding to the response time set from the input of the sample injection timing signal 8, in a manner similar to the foregoing embodiment.

Also in this embodiment, even if the setting of the response time is frequently changed for adjusting a noise reduction effect, the holding time in a data processor 7 never varies. Additionally, in this embodiment, it is also possible to simultaneously treat a signal desirably synchronized with the injection of a sample (when gradient elution is started or the like), thus making the present invention effective in such a case where components of a mobile phase are changed during analysis.

Figure 4:
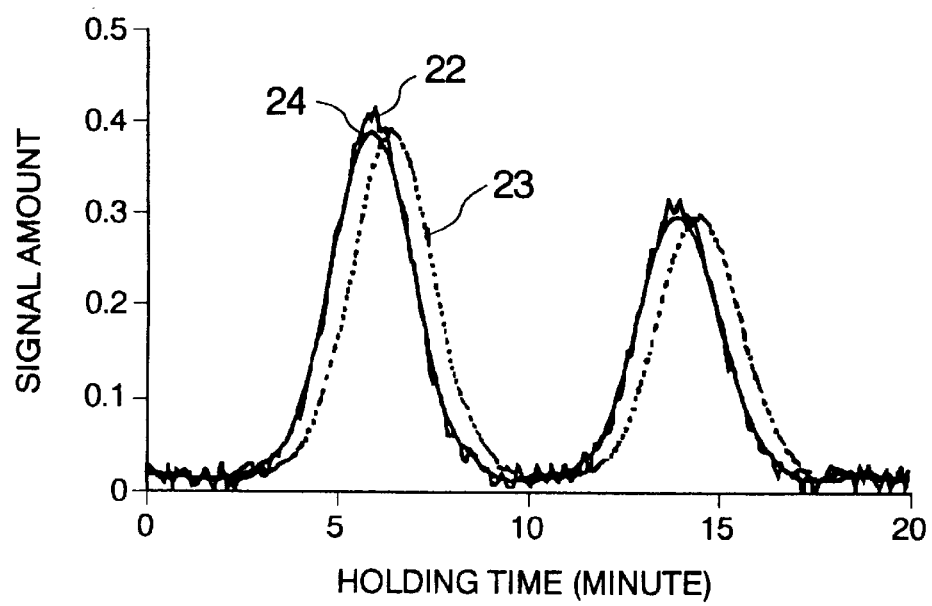
FIG. 4 is a graph illustrating a chromatogram provided by the embodiment of the present invention in comparison with that of a prior art example.

FIG. 4 illustrates a chromatogram provided by the embodiment of the present invention in comparison with that of a prior art example.

A curve 22 indicates a chromatogram derived without any noise reduction processing. In contrast with this chromatogram 22, a curve 23 indicates a chromatogram which is derived with noise reduction processing in accordance with a moving average method but not with the processing of the present invention. While noise is reduced in the chromatograph 23, the positions of peaks are different from those of the chromatogram 22, and the holding time is entirely shifted. A chromatogram derived by implementing the present invention is indicated by a curve 24. The chromatogram 24 exhibits reduced noise and the peaks substantially at the same positions as those of the chromatogram 22.

According to the present invention as described above, it is possible to realize a chromatograph which is free from any change in holding time even if a moving average method is used for noise reduction. It is also possible to realize a chromatograph which permanently eliminates a delay in holding time even if a noise reduction effect is changed.

It will therefore be appreciated from the foregoing that the present invention provides a chromatograph which is capable of accurately identifying components of a sample even if a moving average method is used for noise reduction.

What is claimed is:

1. A chromatograph including a pump which supplies a mobile phase to a column and a sample injector which injects a sample into the column to separate the sample into components by the column, a detector which detects the separated components to generate an electric signal, and a data processor which applies a moving average calculation to the electric signal, and executes processing for deriving data related to a chromatogram based on the averaged electric signal, wherein the start of said processing is delayed by a time equal to a delay time occurring when generating said averaged electric signal, said delay time caused by said moving average calculation.

2. A chromatograph comprising:

a column;

means for supplying a mobile phase to said column;

means for injecting a sample into said column such that said sample is separated into components by said column;

means for detecting said separated components to generate an electric signal, and applying a moving average calculation to said electric signal;

means for executing processing for deriving data related to chromatogram data based on said moving-averaged signal; and means for generating a data processing start signal for starting said processing with a delay corresponding to a delay time for generating said averaged electric signal, said delay time caused by said moving average calculation, wherein said processing is executed based on said data processing start signal.

3. A chromatograph according to claim 2, further comprising means for setting a condition for said moving average calculation for said generated signal, wherein said data processing start signal is automatically generated with a delay corresponding to the delay time for generating said averaged signal, said delay time being determined by said set moving average condition.

4. A chromatograph according to claim 2, wherein said data processing start signal is generated by said electric signal generating and averaging means.

5. A chromatograph according to claim 2, further comprising a controller for said electric signal generating and averaging means, wherein said data processing start signal is generated by said controller.

6. A chromatograph comprising:

a column;

means for supplying a mobile phase to said column;

means for injecting a sample into said column such that said sample is separated into its components by said column and for generating a sample injection signal;

means for detecting said separated components to generate an electric signal, sampling said electric signal at regular intervals to convert said electric signal to a digital signal, and averaging digital samples at a predetermined number of sampling points before and after each sampling point;

means for executing processing for deriving data related to chromatogram data based on said averaged signal; and means for generating a data processing start signal for starting said processing with a delay corresponding to a delay time for generating said averaged electric signal, said delay time caused by said moving average technique, wherein said processing is executed based on said data processing start signal.

* * * * *